United States Patent [19]
Courtney et al.

[11] Patent Number: 6,072,029
[45] Date of Patent: Jun. 6, 2000

[54] DERIVATIVES OF HUMAN $\alpha_1$-ANTITRYPSIN AND PROCESS FOR THEIR PREPARATION

[75] Inventors: Michaël Courtney, Brumath; Luc-Henri Tessier; Sophie Jallat, both of Strasbourg; Jean-Pierre Lecocq, Reichsteet, all of France

[73] Assignee: Transgene S.A., France

[21] Appl. No.: 07/967,576

[22] Filed: Oct. 27, 1992

Related U.S. Application Data

[63] Continuation of application No. 07/796,887, Nov. 29, 1991, abandoned, which is a continuation of application No. 07/508,468, Apr. 12, 1990, abandoned, which is a continuation of application No. 07/206,429, Jun. 7, 1988, abandoned, which is a continuation of application No. 06/848,402, Feb. 13, 1986, abandoned.

[30] Foreign Application Priority Data

Jun. 19, 1984 [FR] France ................................. 84 09592
May 15, 1985 [FR] France ................................. 85 07393
Jun. 18, 1985 [WO] WIPO ................... PCT/FR85/00158

[51] Int. Cl.$^7$ ................. C07K 1/00; C07K 14/00
[52] U.S. Cl. .................... 530/350; 530/402; 530/808
[58] Field of Search ..................... 530/350, 402, 530/808, 825; 514/2, 12, 822, 870; 435/172.3, 69.1, 69.2

[56] References Cited

U.S. PATENT DOCUMENTS

| | | | |
|---|---|---|---|
| 4,711,848 | 12/1987 | Insley et al. | 435/69.2 |
| 4,732,973 | 3/1988 | Barr et al. | 530/350 |
| 4,752,585 | 6/1988 | Koths et al. | 435/172.3 |

FOREIGN PATENT DOCUMENTS

| | | |
|---|---|---|
| 0103409 | 3/1984 | European Pat. Off. . |
| 0155188 | 9/1985 | European Pat. Off. . |
| 8600337 | 1/1986 | WIPO . |

OTHER PUBLICATIONS

Nakajima et al; Mapping the Extended Substrate Binding Site of Cathepsin G and Human Leukocyte Elastase; The Journal of Biological Chemistry; vol. 254, No. 10, May 25, 1979, pp. 4027–4032.

Hubbard et al; Oxidants Spontaneously Released by Alveolar Macrophages of Cigarette Smokers Can Inactivate the Active Site $\alpha 1$–Antitrypsin, Rendering it Ineffective as an Inhibitor of Neutrophil Elastase; The Journal of Clinical Investigation, Inc.; vol. 80, Nov. 1987; pp. 1289–1295.

Jallat et al; Altered specificities of genetically engineered $\alpha_1$ antitrypsin variants; Protein Engineering; 1986, pp. 29–35.

Jallat et al., Protein Engineering, vol. 1, No. 1, pp. 29–35 (1986).

Morii et al., The Journal of Biological Chemistry, vol. 258 No. 21 pp. 12749–12752 (1983).

Inouye et al. Science vol. 221 pp. 59–61 (Jul. 1, 1983).

Biological Abstracts vol. 77 No. 24663 (1984).

Morii et al J. Biochem vol. 83 No. 1 pp. 269–277 (Aug. 5, 1977).

Rosenberg et al. Nature, vol. 312 pp. 77–80 (Nov. 1984).

Courtney et al, Nature, vol. 313 pp. 149–151 (Jan. 1985).

Owen et al., The New England Journal of Med. vol. 309 No. 12 pp. 694–698 (Sep. 1983).

Nakajima et al, The Journal of Biological Chemistry, vol. 254 No. 10 pp. 4027–4032 (1979).

Jallat et al. J. of Cellular Biochemistry, Suppl. p. 94, No. 9 Part B (1985).

Carrell et al. Nature vol. 298 pp. 329–334 (Jul. 1982).

Travis et al. The J. of Biological Chemistry vol. 260, No. 7 pp. 4384–4389 (Apr. 1985).

Behring, LC–Partigen Description.

*Primary Examiner*—Christina Y. Chan
*Attorney, Agent, or Firm*—Cushman Darby & Cushman IP Group of Pillsbury Madison & Sutro LLP

[57] ABSTRACT

The invention relates to an analog of human $\alpha_1$-antitrypsin characterized in that it is all or part of the protein corresponding to human $\alpha_1$-antitrypsin in which, in 358 position, the amino-acid is selected from among arginine and little or non-oxidizable natural amino-acids when they are integrated into a protein.

1 Claim, 18 Drawing Sheets

FIG-1a

```
147
GAG GAT CCC CAG GGA GAT GCT GCC CAG AAG ACA GAT ACA TCC CAC
Glu Asp Pro Gln Gly Asp Ala Ala Gln Lys Thr Asp Thr Ser His
                                    177

CAT GAT CAG GAT CAC CCA ACC TTC AAC AAG ATC ACC CCC AAC CTG
His Asp Gln Asp His Pro Thr Phe Asn Lys Ile Thr Pro Asn Leu
                207

237
GCT GAG TTC GCC TTC AGC CTA TAC CGC CAG CTG GCA CAC CAG TCC
Ala Glu Phe Ala Phe Ser Leu Tyr Arg Gln Leu Ala His Gln Ser
                    267

AAC AGC ACC AAT ATC TTC TTC TCC CCA GTG AGC ATC GCT ACA GCC
Asn Ser Thr Asn Ile Phe Phe Ser Pro Val Ser Ile Ala Thr Ala
        297                                         357

327
TTT GCA ATG CTC TCC CTG GGG ACC AAG GCT GAC ACT CAC GAT GAA
Phe Ala Met Leu Ser Leu Gly Thr Lys Ala Asp Thr His Asp Glu

ATC CTG GAG GGC CTG AAT TTC AAC CTC ACG GAG ATT CCG GAG GCT
Ile Leu Glu Gly Leu Asn Phe Asn Leu Thr Glu Ile Pro Glu Ala
            387

417
CAG ATC CAT GAA GGC TTC CAG GAA CTC CTC CCT.ACC CTC AAC CAG
Gln Ile His Glu Gly Phe Gln Glu Leu Leu Pro Thr Leu Asn Gln
                            447
```

477
CCA GAC AGC CAG CTC CAG ACC ACC GGC AAT GGC CTG TTC CTC
Pro Asp Ser Gln Leu Gln Thr Thr Gly Asn Gly Leu Phe Leu 507                                    537
AGC GAG GGC CTG AAG CTA GTG GAT AAG TTT TTG GAG GAT GTT AAA
Ser Glu Gly Leu Lys Leu Val Asp Lys Phe Leu Glu Asp Val Lys

AAG TTG TAC CAC TCA GAA GCC TTC ACT GTC AAC TTC GGG GAC ACC
Lys Leu Tyr His Ser Glu Ala Phe Thr Val Asn Phe Gly Asp Thr 597                                    627
GAA GAG GCC AAG AAA CAG ATC AAC GAT TAC GTG AAG GAG AAG GGT ACT
Glu Glu Ala Lys Lys Gln Ile Asn Asp Tyr Val Lys Glu Lys Gly Thr

CAA GGG AAA ATT GTG GAT TTG GTC AAG GAG CTT GAC AGA GAC ACA
Gln Gly Lys Ile Val Asp Leu Val Lys Glu Leu Asp Arg Asp Thr 687                                    717
GTT TTT GCT CTG GTG AAT TAC ATC TTC TTT AAA GGC AAA TGG GAG
Val Phe Ala Leu Val Asn Tyr Ile Phe Phe Lys Gly Lys Trp Glu

747
AGA CCC TTT GAA GTC AAG GAC ACC GAG GAA GAG GAC TTC CAC GTG
Arg Pro Phe Glu Val Lys Asp Thr Glu Glu Glu Asp Phe His Val

```
777  GAC CAG GTG ACC ACC GTG AAG GTG CCT ATG ATG AAG CGT TTA GGC
     Asp Gln Val Thr Thr Val Lys Val Pro Met Met Lys Arg Leu Gly

ATG TTT AAC ATC CAG CAC TGT AAG AAG CTG TCC AGC TGG GTG CTG
                                    807
     Met Phe Asn Ile Gln His Cys Lys Lys Leu Ser Ser Trp Val Leu

867  CTG ATG AAA TAC CTG GGC AAT GCC ACC GCC ATC TTC TTC CTG CCT
     Leu Met Lys Tyr Leu Gly Asn Ala Thr Ala Ile Phe Phe Leu Pro
                                    897

GAT GAG GGG AAA CTA CAG CAC CTG GAA AAT GAA GAC AGA AGG TCT GCC AGC
     Asp Glu Gly Lys Leu Gln His Leu Glu Asn Glu Asp Arg Arg Ser Ala Ser

957  ATC ATC ACC AAG TTC TTG GAA AAT GAA GAC AGA AGG TCT GCC AGC
                                    987
     Ile Ile Thr Lys Phe Leu Ser Ile Thr Gly Thr Tyr Asp Leu Lys

TTA CAT TTA CCC AAA CTG TCC ATT ACT GGA ACC TAT GAT CTG AAG
                    1017
     Leu His Leu Pro Lys Leu Ser Ile Thr Gly Thr Tyr Asp Leu Lys

1047 AGC CTC CTG GGT CAA CTG GGC ATC ACT AAG GTC TTC AGC AAT GGG
                                    1077
     Ser Leu Leu Gly Gln Leu Gly Ile Thr Lys Val Phe Ser Asn Gly
```

```
1107
GCT GAC CTC TCC GGG GTC ACA GAG GAG GCA CCC CTG AAG CTC TCC
Ala Asp Leu Ser Gly Val Thr Glu Glu Ala Pro Leu Lys Leu Ser 1137                                            1167
AAG GCC GTG CAT AAG GCT GTG CTG ACC ATC GAC GAG AAA GGG ACT
Lys Ala Val His Lys Ala Val Leu Thr Ile Asp Glu Lys Gly Thr

1197
GAA GCT GCT GGG GCC ATG TTT TTA GAG GCC ATA CCC ATG TCT ATC
Glu Ala Ala Gly Ala Met Phe Leu Glu Ala Ile Pro Met Ser Ile 1227                                            1257
CCC CCC GAG GTC AAG TTC AAC AAA CCC TTT GTC TTC TTA ATG ATT
Pro Pro Glu Val Lys Phe Asn Lys Pro Phe Val Phe Leu Met Ile

1287
A CAA AAT ACC AAG TCT CCC CTC TTC ATG GGA AAA GTG GTG AAT
  Gln Asn Thr Lys Ser Pro Leu Phe Met Gly Lys Val Val Asn 1317                                    1347
CCC ACC CAA AAA TAA
Pro Thr Gln Lys ***

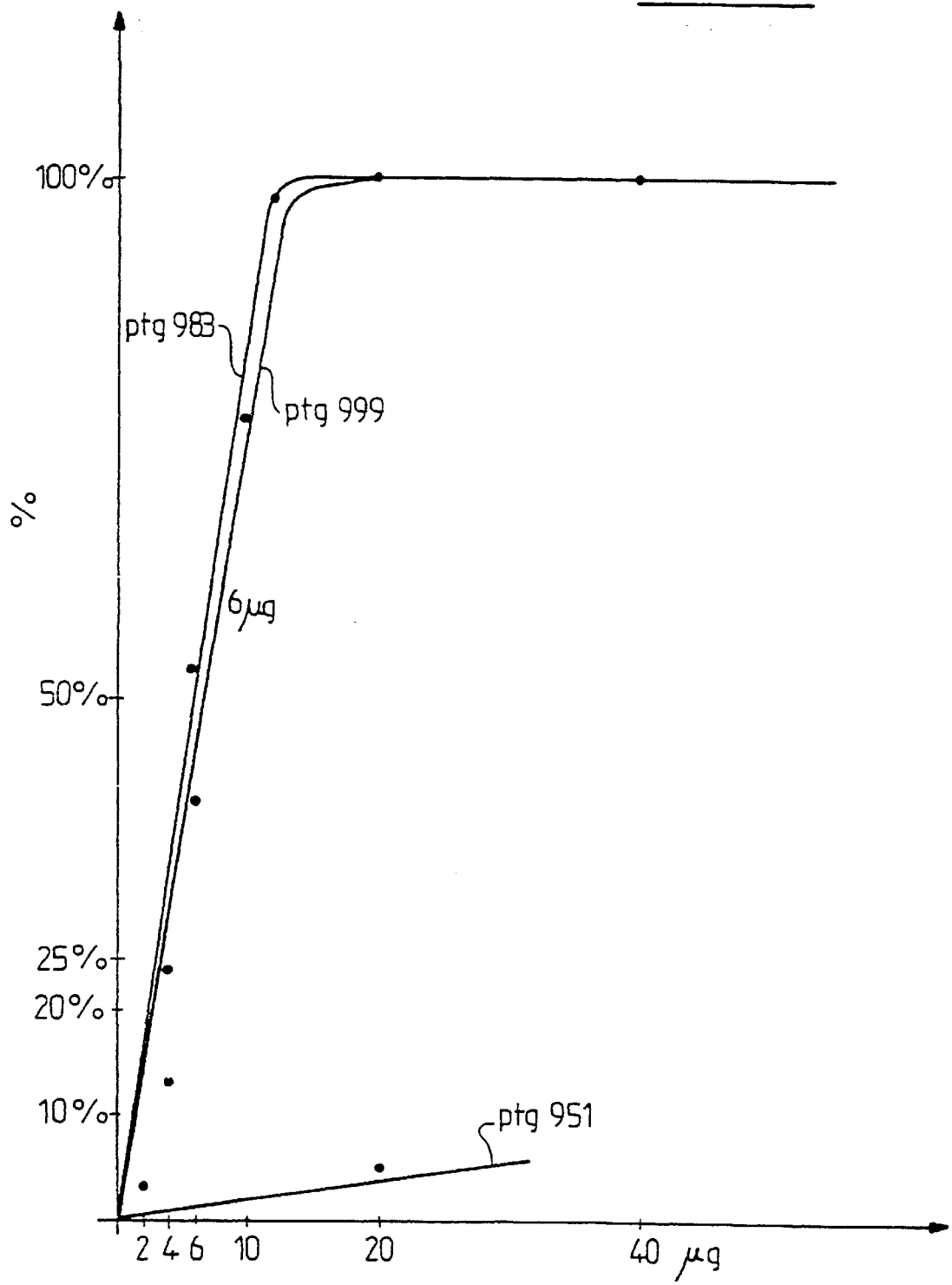

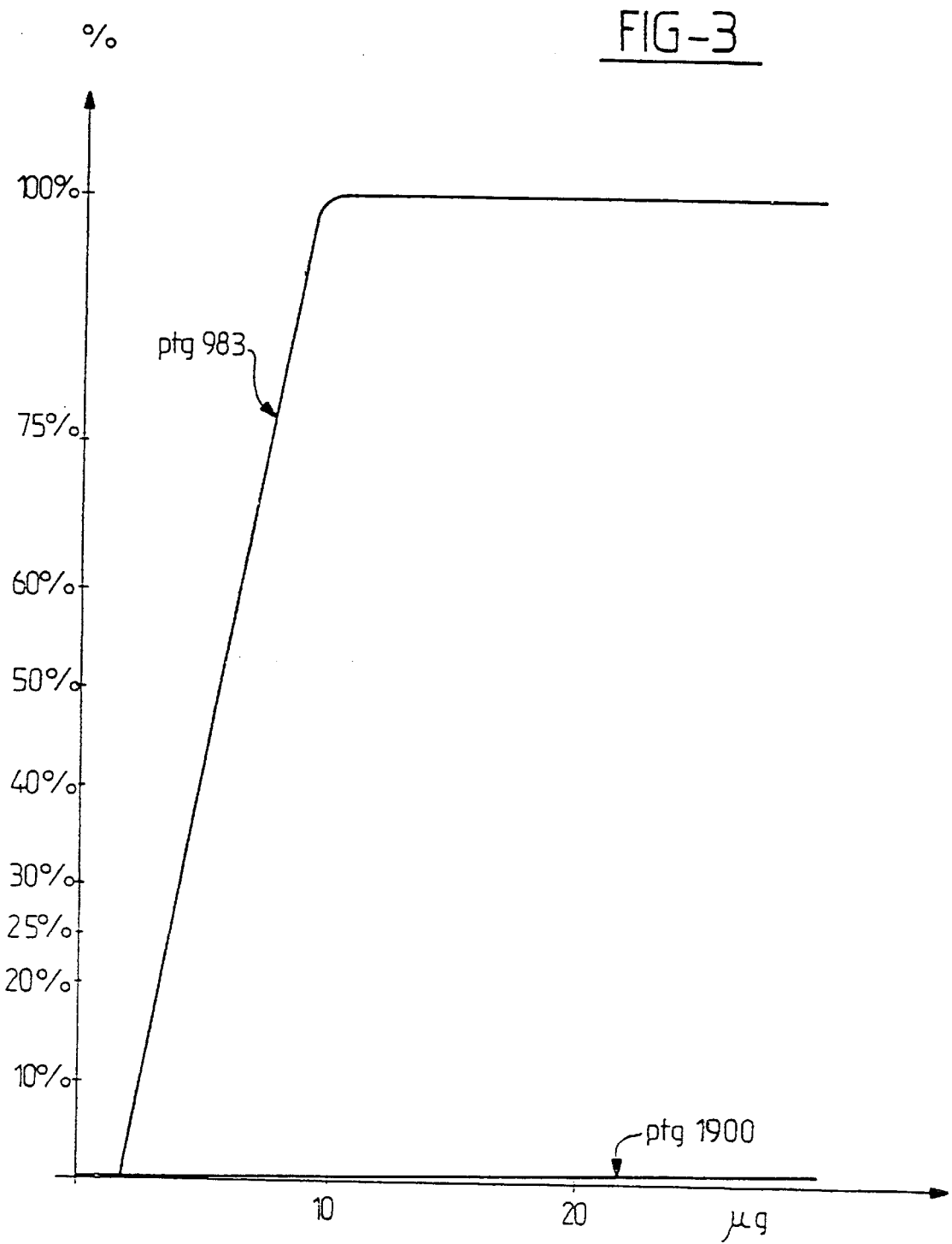

FIG-7
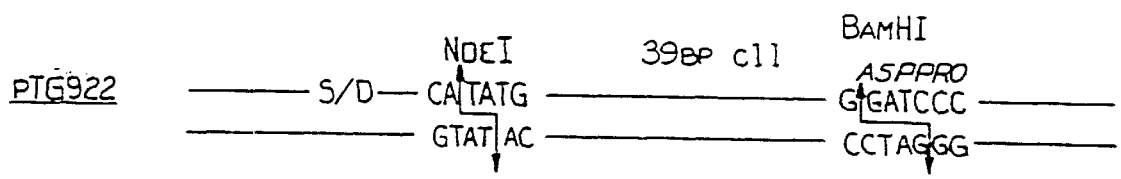
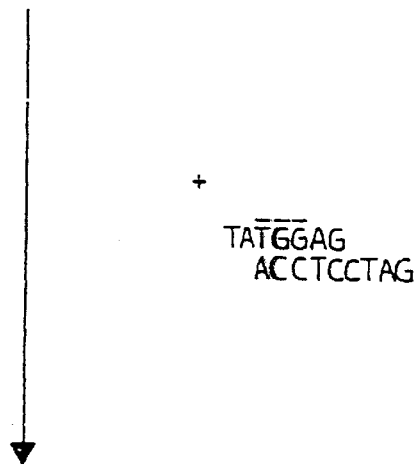
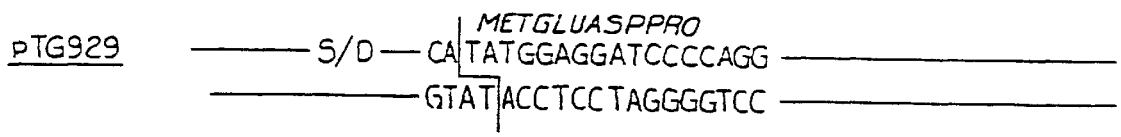
CCTGGGGATCCTCCA

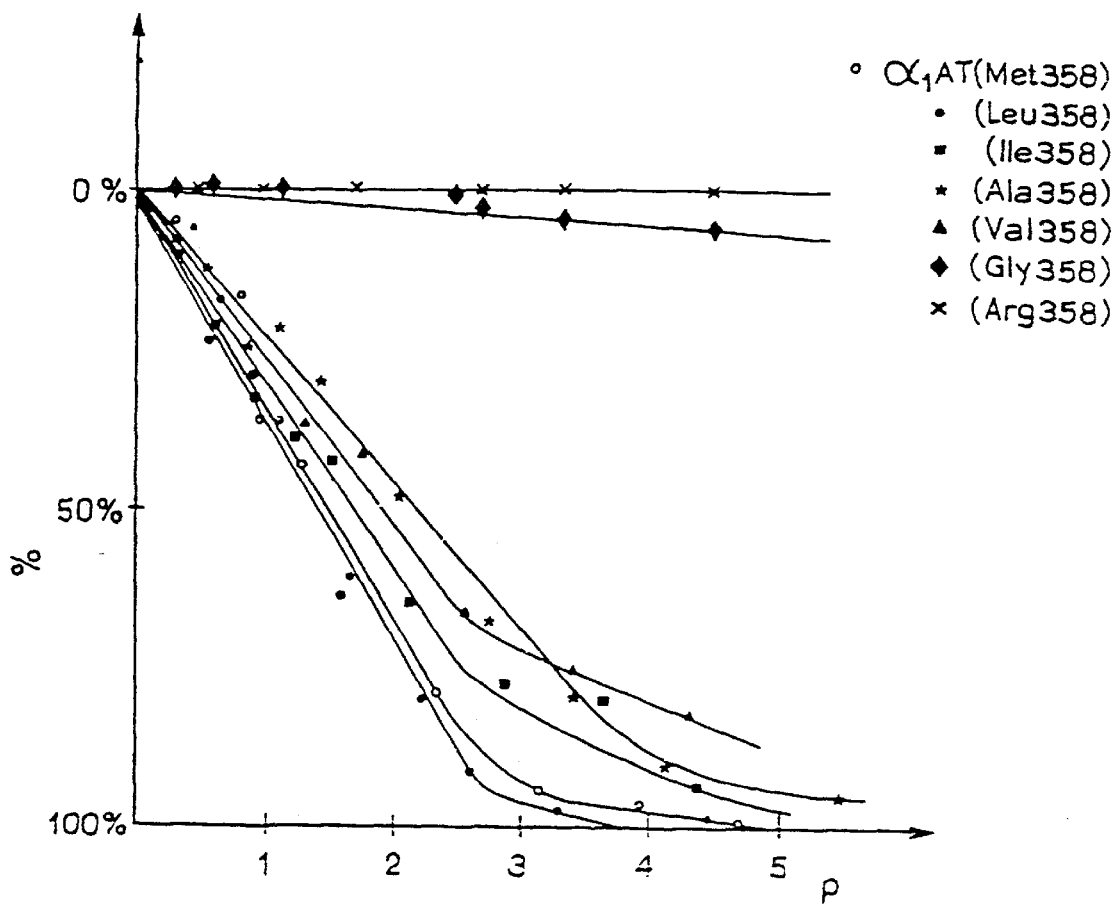
FIG_10

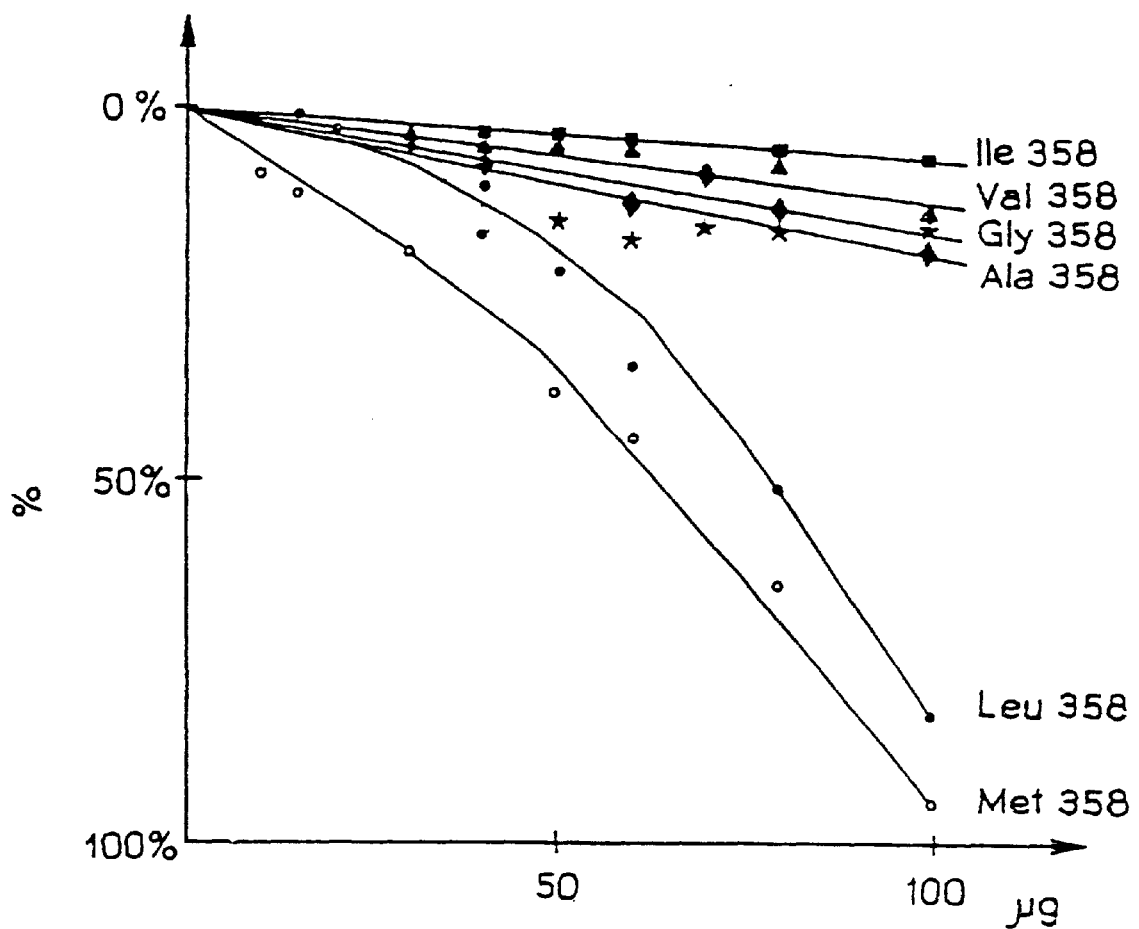
FIG_11

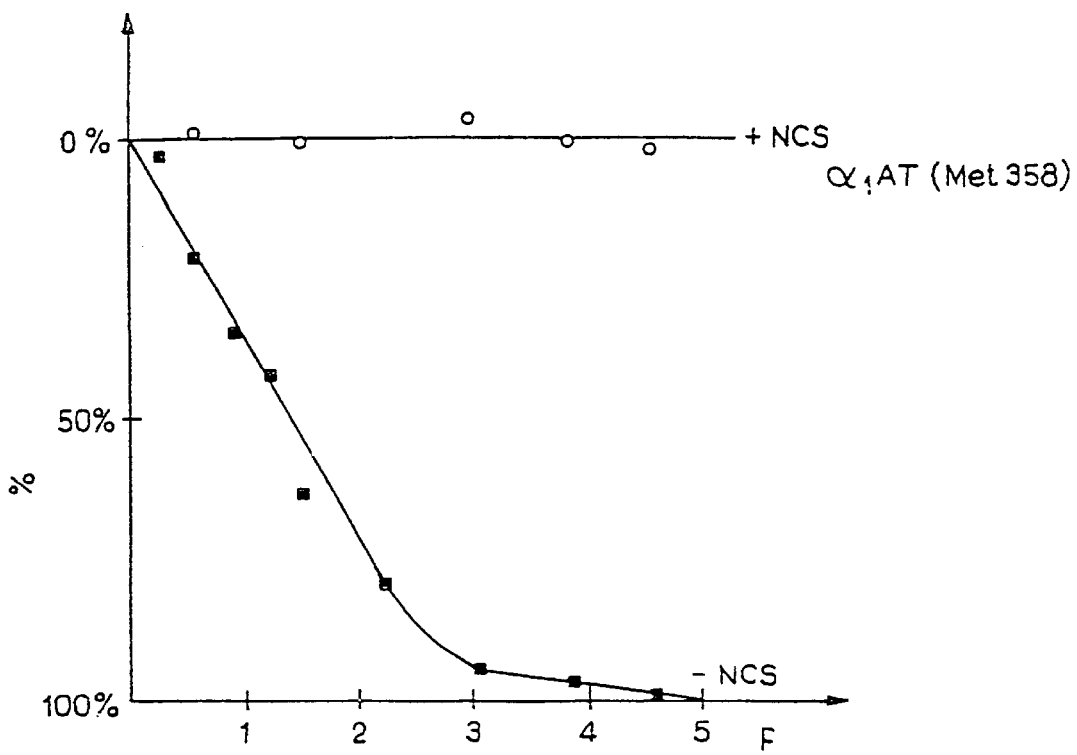
FIG_12 a
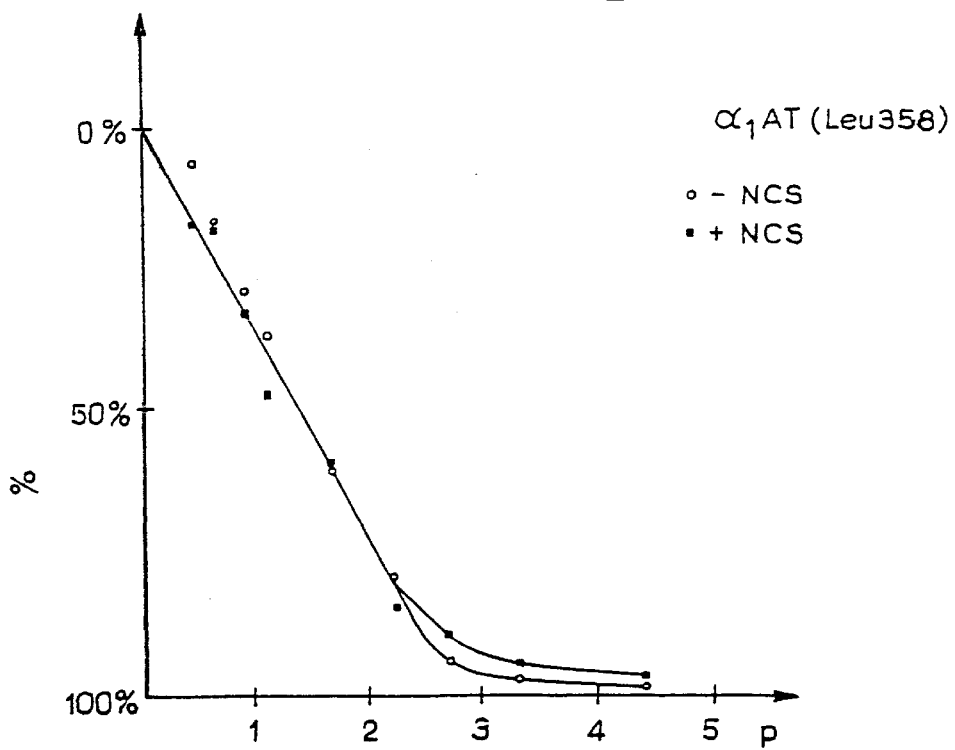
FIG_12 b

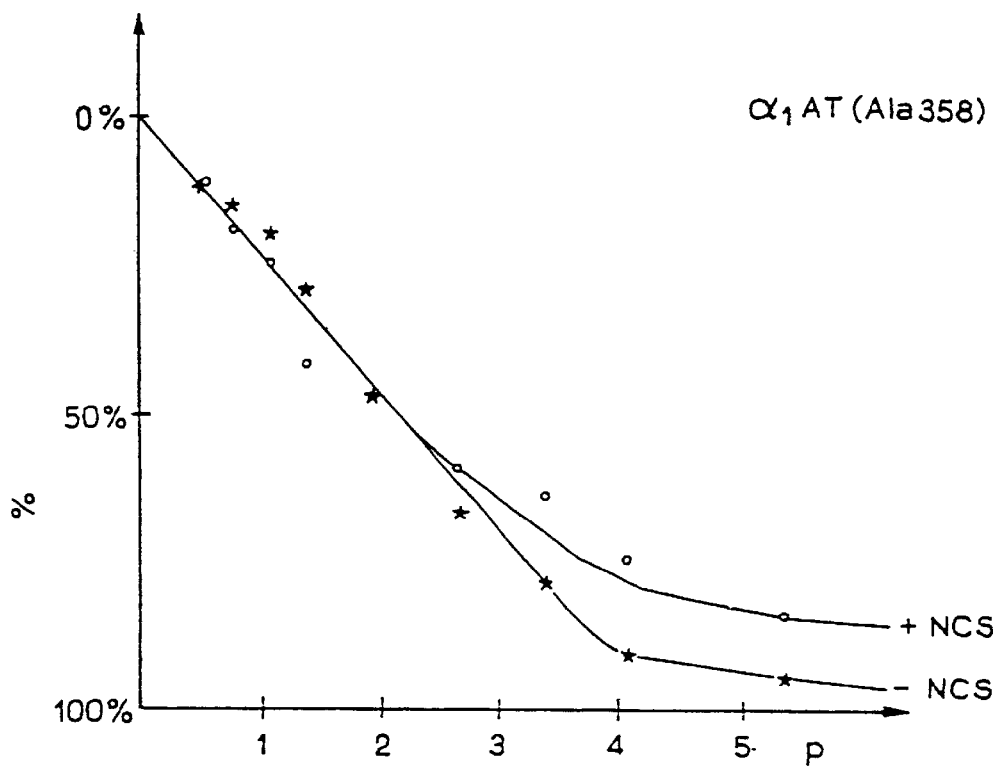
FIG_12c
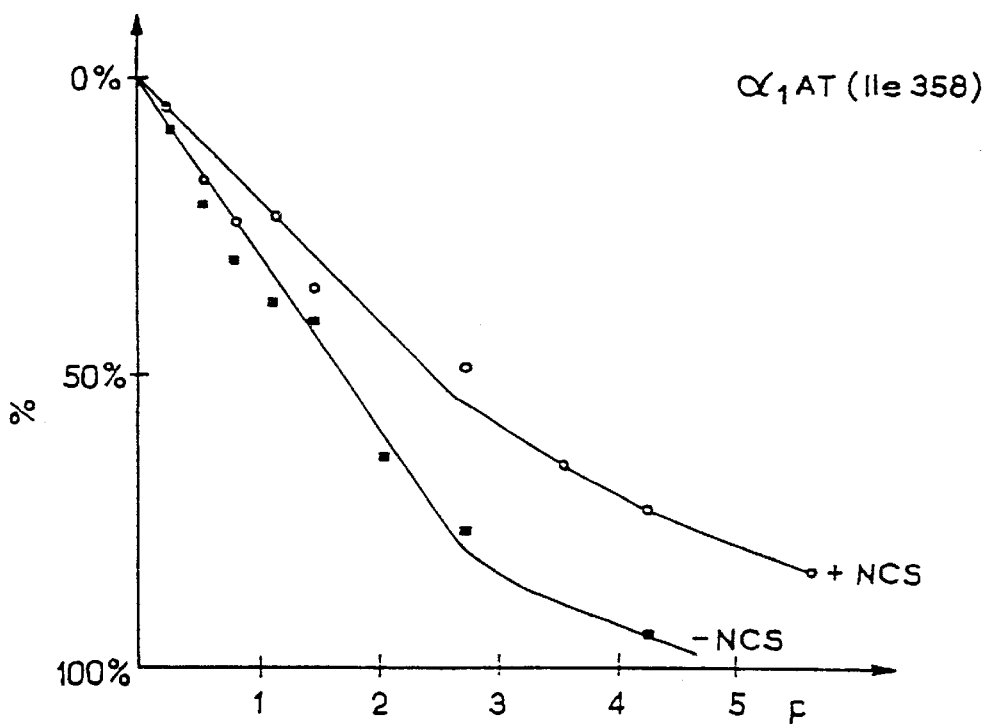
FIG_12d

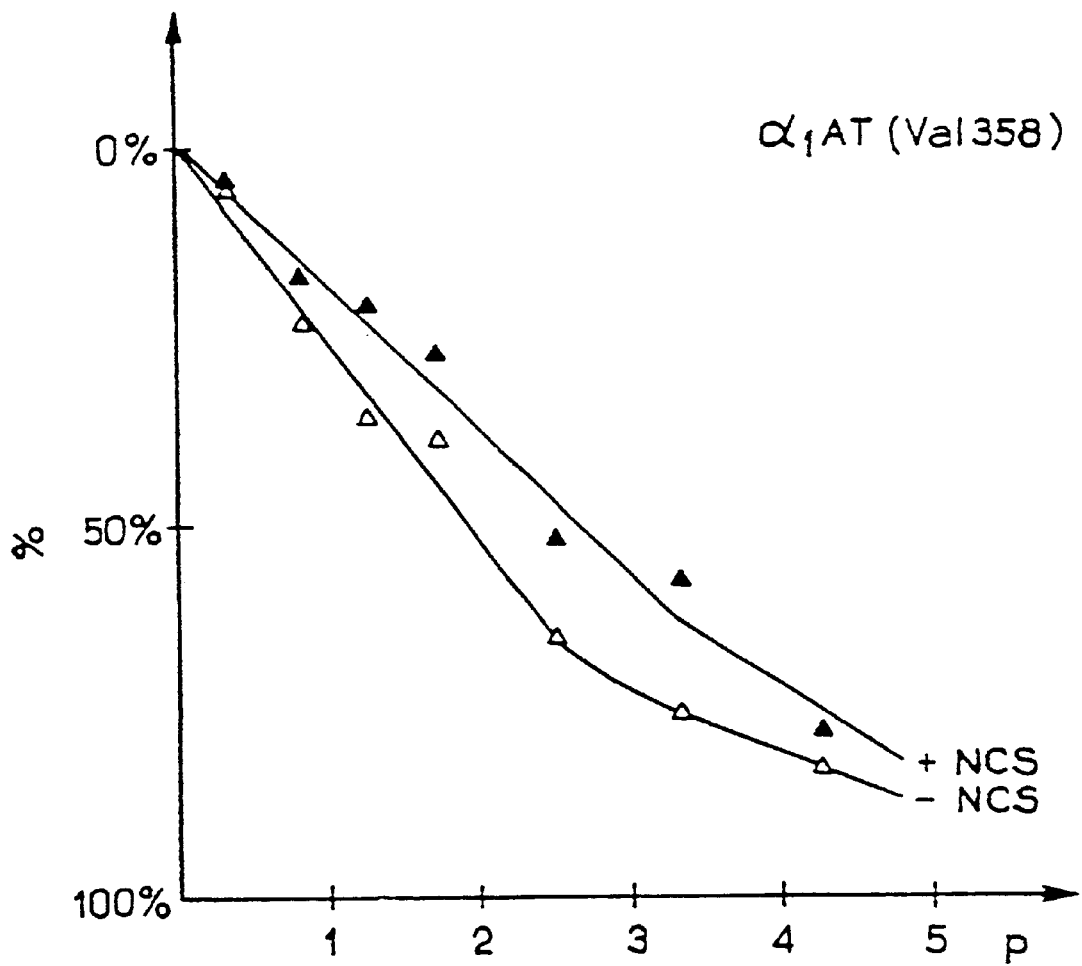
FIG_12e

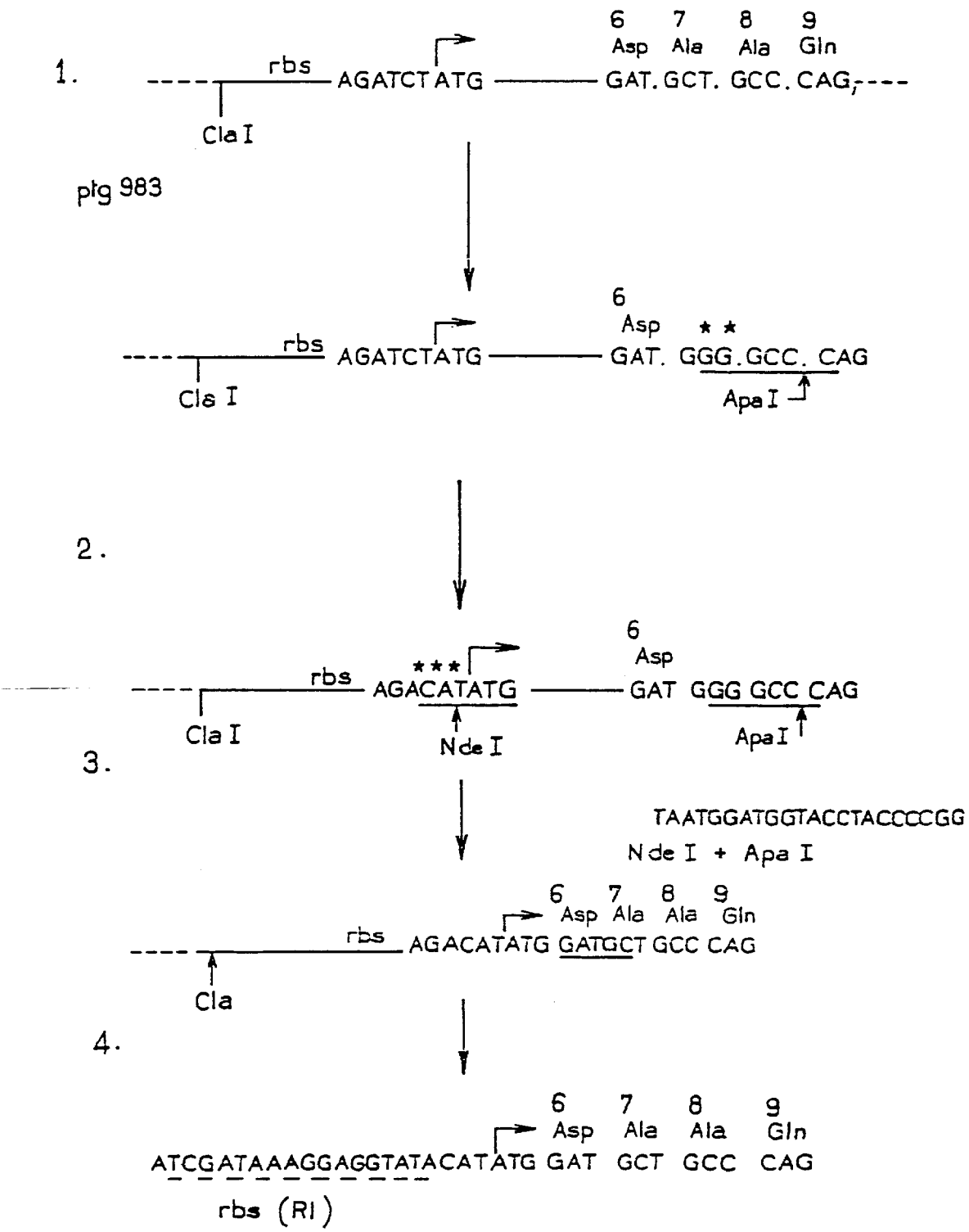
FIG_13

DERIVATIVES OF HUMAN $\alpha_1$-ANTITRYPSIN AND PROCESS FOR THEIR PREPARATION

This application is a continuation of application Ser. No. 07/796,887, filed Nov. 29, 1991, now abandoned, which is a continuation of application Ser. No. 07/508,468, filed Apr. 12, 1990, now abandoned, which is a continuation of application Ser. No. 07/206,429, filed Jun. 7, 1988, now abandoned, which is a continuation of application Ser. No. 06/848,402, filed Feb. 13, 1986, now abandoned.

The present invention relates to analogs of human $\alpha_1$-antitrypsin as well as processes for their preparation and pharmaceutical compositions containing these compounds.

As has been described in French patent application in the name of Applicant n° 83 00909 and in the corresponding European patent n° 84 400126 it is possible to prepare human $\alpha_1$-antitrypsin by genetic engineering techniques.

This patent application develops very broadly the possible applications of this compound.

A closer study of the activity of human $\alpha_1$-antitrypsin has enabled the interest that analogs of this product could present, to be established.

The most important physiological role of $\alpha_1$-antitrypsin is the inhibition of neutrophil elastase in the lower portion of the respiratory tract.

In healthy lungs, the $\alpha_1$-antitrypsin and the elastase act in balanced manner to create an area of localised liquefaction around foreign bodies before their ejection.

A defect in this equilibrium in favour of the elastase leads to an uncontrolled action of the protease and very considerable damages in the tissues. This leads clinically to emphysema.

Such an unbalance appears in the case of hereditary deficiency of $\alpha_1$-anti-trypsin.

The most frequent cause of non-hereditary emphysema is cigarette smoke. In this case there is an interaction of various factors which lead to an alveolar-protease/anti-protease unbalance. The activity of the $\alpha_1$-antitrypsin is reduced by oxidation, either directly by the cigarette smoke itself, or by the oxygen radicals which are released by the macrophages drawn to the lung by the presence of polluting smoke particles. In addition these macrophages (which themselves produce an elastase) secrete a chemotactic factor which results in a release of neutrophil elastase at the site.

It is also probable that the $\alpha_1$ antitrypsin becomes sensitive to an irreversible inactivation by proteolytic cleavage. Thus, in lungs of heavy smokers there exists a charge of elastase which can lead to a destructive disease of the lungs.

If, as has been described in the preceding French patent application, it is possible to use bacterial $\alpha_1$-antitrypsin (called below $\alpha_1$-AT) to treat unbalances of all orders mentioned previously, it seems none the less that it would be interesting to provide an analog of $\alpha_1$-AT having an improved in vivo stability.

This is why the present invention particularly proposes analogs of $\alpha_1$-AT having improved in vivo stability, in particular an increased resistance to oxidation.

Numerous studies have shown that inactivation of $\alpha_1$-AT is probably due to oxidation of the methionine residue at the 358 position which is found situated at the fixation site of the elastase.

The present invention therefore relates to the preparation in bacteria, particularly in *Escherichia coli*, of a human $\alpha_1$-AT which contains, in place of the amino-acid methionine at the 358 position, a non-oxidizable amino-acid such as valine, as well as the corresponding analogs of $\alpha_1$-AT.

The studies carried out on the fixations of the elastase to various substrates indicate that the change of the methionine into valine improves the association constant between $\alpha_1$-AT and the elastase and increases the activity of the analog.

In addition, $\alpha_1$-AT inhibits a larger amount of serine proteases including elastase, trypsin, chimo-trypsin, plasmin and thrombin. Its most important function, as has been previously indicated, is to be an inhibitor of the neutrophile elastase in the respiratory tract.

The role of $\alpha_1$-AT in the clotting process is suggested by its capacity to inhibit thrombin. This enzyme is responsible for the cleavage of fibrinogen into fibrin, which is the final step in the blood coagulation cascade.

The thrombin also triggers the platelet aggregation and catalyses the activation of factor V, factor VIII and factor XIII.

The inactivation of thrombin by $\alpha_1$-AT is a complex process. In a molar ratio of 1:1, the inactivation is weak and incomplete, but by increasing the molar excess of the $\alpha_1$-antitrypsin, the inhibition ratio increases and thrombin is completely inhibited. However, as no hypercoagulability symptom is observed in the case of $\alpha_1$-antitrypsin deficient homozygote, it seems certain that the $\alpha_1$-antitrypsin does not play an essential part in the control of blood coagulation.

The anti-thrombin activity level in human plasma may be attributed completely to the account of the activity of the anti-thrombin III (AT-III) and the $\alpha^2$-macroglobulin.

In a recent publication, an $\alpha_1$-antitrypsin mutant ($\alpha_1$-AT Pittsburgh) has been described which contains a change of a single nucleotide replacing the methionine by arginine at the level of the position 358 reactive site of the molecule. This $\alpha_1$-AT variant has been responsible for a tragic disturbance resulting in the death of a patient of 14 years. This $\alpha_1$-AT mutant no longer behaves as an inhibitor of elastase but shows an anti-thrombin activity increased by several hundred-fold. This activity is independant of the action of heparin.

These observations may be explained by comparison of the amino-acid sequence of $\alpha_1$-AT and AT-III. These protease inhibitors show 29% of common structure indicating that they both come from a common protein.

Their reactive center shows a similar sequence; at the central position of the $\alpha_1$-antitrypsin is seen a methionine residue , which is the preferred cleavage site for elastase, on the other hand at the same place AT-III has an arginine residue, which is the preferred site for thrombin.

Thus, in $\alpha_1$-AT Pittsburgh, a substitution of the methionine by arginine leads to an alteration of the specificity of the inhibition with respect to the elastase to transfer it to the thrombin.

The present invention therefore relates, firstly, to analogs of human $\alpha_1$-AT in which, in the protein corresponding to all or part of an $\alpha_1$-AT, the aminoacid at the 358 position (normally methionine) is replaced by arginine or an amino-acid which is not oris little oxidizable in vivo, that is to say particularly glycine, alanine, valine, isoleucine, leucine, phenylalanine.

In the present description, by "an $\alpha_1$-AT" will be meant one of the various natural variants of this protein although their structures are not all known.

The numbering of the amino-acids is that commonly accepted, the first amino-acid being Glutamine in the publications of Kurachi et coll. and Chandra et coll (FIG. 1).

More precisely, the amino-acid 358 is found in the fixation region of the elastase and in the compounds of the invention this region has preferably the following structure:

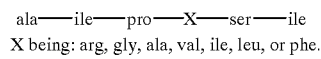

X being: arg, gly, ala, val, ile, leu, or phe.

Of course, the expression "an $\alpha_1$-AT" also denotes punctual mutants in which a mutation has been able to intervene in an unreactive site ; this mutation may, in particular, intervene in the preparation of analogs by the techniques of punctual mutations of the genes.

Among the analogs according to the invention, two are particularly interesting:

[$Arg^{358}$] $\alpha_1$-AT and

[$Val^{358}$] $\alpha_1$-AT.

In addition, recent studies have established that normal plasmatic $\alpha_1$-AT is present in two forms, one form which has been described previously and another form which includes an N-terminal deletion of 5 amino-acids.

This is why the present invention relates also to derivatives of $\alpha_1$-AT or analogs of $\alpha_1$-AT such as previously described, characterized in that the sequence of the $\alpha_1$-AT or of its analogs has been truncated by its 5 N-terminal amino-acids.

According to studies underway, it seems that the truncated form comes from a rearrangement of the native molecule in the plasma. The truncated form is present in a concentration about 10 times weaker than the native form.

The tests carried out on these truncated variants show that they are effective inhibitors of elastase like the native protein.

The present invention also relates to a process for the preparation of analogs of $\alpha_1$-AT in which a host cell is cultivated, particularly a microorganism, comprising an expression vector of the DNA sequence coding for the $\alpha_1$-AT in which the codon corresponding to the amino-acid 358 of the mature protein codes for arg or an unoxidizable natural amino-acid when it is integrated into a protein or indeed in which the DNA sequence coding for the $\alpha_1$-AT or its analogs has been deleted of 15 bases at the 5' end.

The nature of the expression vector depends obviously on the microorganism used.

In the case where the microorganism is a bacterium, particularly *E. coli*, the vector will preferably be a plasmid comprising a replication origin in *E. coli*, for example the replication origin of pBR322.

The expression plasmids for the gene of the $\alpha_1$-AT in bacteria are described in European patent n° 84 400126 in the name of Applicant as well as in Belgian patent n° 895 961.

Among the bacterial vector plasmids, it is preferred to use those including a promoter of the λ phage, the $P_L$ promoter, and a fixation site of the ribosomes of the protein cII of λ: cII rbs or a synthetic site such is described in European patent n° 84 400126.

In addition, these plasmids can comprise all or part of the N gene. Other characteristics of these plasmids are demonstrated in the examples and the previously cited patent.

In the case where the microorganism is a yeast, it is possible to use as a vector plasmid the vectors described in the European patent n° 0 103 409. When the yeast is a strain of *Saccharomyces cerevisiae*, the vector will include, preferably, a replication origin of the 2μ plasmid, and a yeast promoter among those described in said patent application.

Generally, the precise structure of the expression vector does not constitute an essential characteristic of the present invention.

The sequence coding for the analog of $\alpha_1$-AT may be prepared by techniques known from the sequence of naturals $\alpha_1$-AT of a clone.

It is possible to replace by restriction-ligation, the portion of the gene which it is desired to modify by a synthetic gene including the sequence coding for the desired analog.

However, it is also possible to proceed by punctual mutation, in particular when the codon of the analog only differs from a nucleotide with respect to the codon of the methionine: ATG, this is, for example, the case of val : GTG, of arg: AGG or of leucine, of isoleucine or of phenylalanine.

This punctual mutation technique will be described in detail in the examples.

Clones of $\alpha_1$-AT, as well as their preparations, are known and described in the publications of Kurachi et coll. and Chandra et coll., as well as in the various patents and patent applications mentioned previously.

The techniques employed in these processes are known in principle and/or described in the cited documents.

Transformation of strains by vectors as well as the conditions of culture of the transformants in order to obtain the analogs of $\alpha_1$-AT are also known and are a function of the microorganisms employed.

The $\alpha_1$-AT analogs according to the invention, whether truncated or not,may be used as a medicament, preferably in place of $\alpha_1$-AT in the treatment of $\alpha_1$-AT deficiencies, inherited or not the $\alpha_1$-AT analogs may be used, for example, in the treatment and prevention of pulmonary emphysemas.

The analog including an arginine at the 358 position is an anticoagulant and will be more particularly usable as an anticoagulant medicament but could also be used in laboratories treating, assaying or stocking blood.

For example, this analog could be used in the treatment and prevention of thromboses and in micro-surgery to reduce swelling.

One of the advantages of this analog of $\alpha_1$-AT is that, as distinct from heparin, it seems to act directly and not through a component like AT-III; now, in the case of operation shock, a lowering of AT-III is often noted, under these conditions heparin cannot play its role as anticoagulant as distinct from the analog of $\alpha_1$-AT.

For the laboratory applications, the analog of $\alpha_1$-AT may be used for example in extracorporal or blood assays.

The various modifications of the present invention are also usable as biological reagents, particularly for the assay of neutrophil elastase and thrombin.

In particular the variants [$Leu^{358}$] $\alpha_1$-AT and [$Met^{358}$] $\alpha_1$-AT are useful as inhibitors of cathepsin G.

The useful dosages depend, of course, very largely on the type of disorder to be treated and on the exact nature of the analog to be employed and must be adapted by methods known to the technician in the art.

In the same way, the precise nature of the pharmaceutical compositions will depend on the application route envisaged and does not constitute a characteristic of the present invention.

Finally, these various compounds may be used in immobilised form on a suitable support such as beads or tubes, for example.

The examples below are intended to demonstrate other features and advantages of the present invention.

BRIEF DESCRIPTION OF THE DRAWINGS

The accompanying figures are the following:

FIGS. 1*a* –1*d* are the sequence of the cDNA of a human gene coding for the $\alpha_1$-AT.

FIG. 2 shows the anti-elastase activity of the product obtained from *E. coli*/pTG999.

FIG. 3 shows the anti-elastase activity of the *E. coli*/pTG1900 extracts.

FIG. 7 shows diagramatically the preparation of pTG929.

FIG. 9 shows diagramatically the technique of the preparation of the variants by replacement of the appropriateDNA fragment in the gene of $\alpha_1$-AT.

FIG. 10 shows the variation of the % inhibition of human neutrophil elastase for different variants.

FIG. 11 represents the variation of the percentage inhibition of human cathepsin G for various variants.

FIGS. 12a to 12e represent the percentages of elastase inhibition for the variants after treatment with NCS.

FIG. 13 shows diagramatically the preparation of the truncated variants.

EXAMPLE 1—[Val$^{358}$] $\alpha_1$-AT

Figure 4:
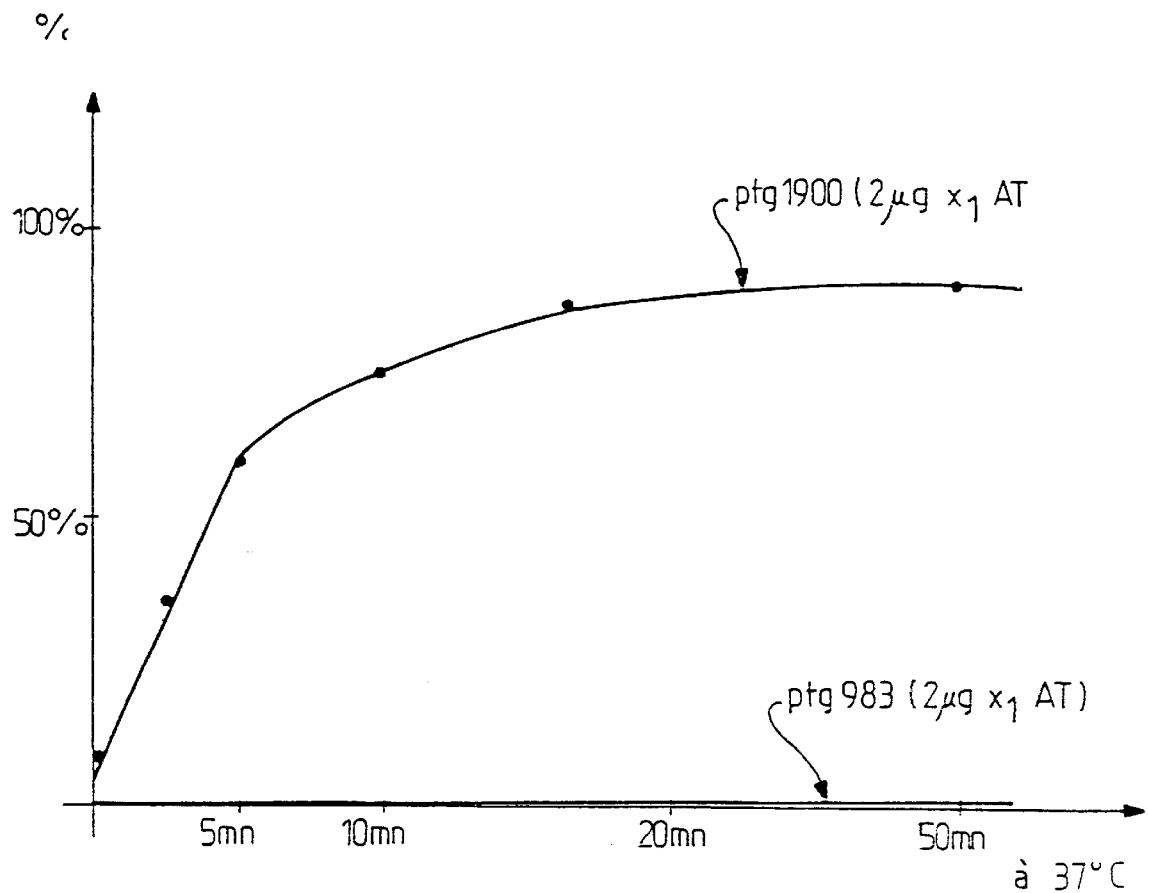
FIG. 4 represents the anti-thrombinic activity of the *E. coli*/pTG1900 extracts.

Direct Mutagenesis in Vitro of the Gene of Human $\alpha_1$-AT

The mutation replacing the methionine by valine necessitates the change of a single base (ATG gives GTG). A direct mutagenesis of the site may be obtained by employing a synthetic oligonucleotide (bearing the mutated version of the sequence) which may, firstly, be hybridized with a model of the single-strand gene, then act as an initiator for the synthesis of the supplementary strand by means of the polymerase DNA.

In this way, a double strand sequence is obtained, one of the strands including the sequence corresponding to the wild type, the other to the mutated sequence.

If a genome of M13 containing the gene of the single-strand $\alpha_1$-AT is used as a model, the double strand molecule obtained will be utilisable to transform the *E. coli* host cells and the phages containing the mutant gene will be identifiable by screening of the plates.

The cloning of the cDNA of human $\alpha_1$-AT and its expression in *E. coli* have already been described, for example in the previously mentioned patents and by Courtney et coll. 1984.

A clone producing $\alpha_1$-AT, pTG983, produces biologically active $\alpha_1$-AT at a level corresponding to about 1% of the total cell proteins of *E. coli*.

To mutate the sequence of $\alpha_1$-AT, a fragment ClaI-PstI, containing the gene, obtained from pTG983 is transferred into the vector M13, M13mp701, between the sites AccI and PstI.

The single-strand coding DNA is then isolated from the phage particle obtained after infection of the host cell *E. coli* JM103. The oligonucleotide 5'-ATAGACACGGTATG-3' (synthesized chemically) is hybridized with a model DNA in a molar excess of 100 times by heating to 100° C. for 5 minutes then by slow cooling to 4° C. This oligonucleotide is complementary to the region of the active site of $\alpha_1$-AT but contains a valine codon in place of the methionine codon:

|  | ala | ile | pro | met | ser | ile |
|---|---|---|---|---|---|---|
| original sequence: | GCC | ATA | CCC | ATG | TCT | ATC |
|  | ala | ile | pro | val | ser | ile |
| mutated sequence: | GCC | ATA | CCC | GTG | TCT | ATC |

Synthesis of the second strand is then carried out by incubating the specimen (0.5 pmol. of single-strand DNA) for 2 hours at room temperature with 200 µg/ml of polymerase DNA (Klenow fragment), 40 µ/ml of ligase DNA T4, 0.5 mM of deoxynucleotide triphosphate and 1 mM of ATP in a buffer (8 mM Tris-HCI, pH 7.5/8 mM of MgCl$_2$/40 mM NaCl/6mMβ-mercaptoethanol).

The sample is then heated to 65° C. for 10 minutes, one ligase unit and 1 mM of ATP are then added and incubated again for 16 hours at 40° C. Aliquot parts of the reaction mixture are then used to convert the competent *E. coli* JM 103 cell. Phage areas are marked on LB plates and the resulting colonies absorbed on a nitrocellulose filter and selected to establish the mutant phage by hybridization with mutated oligonucleotide marked with $^{32}$P by using the kinase T4 polynucleotide.

Under suitable conditions, the oligonucleotide forms a hybrid stable only with the completely homologous sequence, that is to say mutated. In this case hybridization in 3×SSC, 1×Denhardt, 0.5% of sodium pyrophosphate, 0.1% SDS at 50° C., results in an effective selection.

The DNA of the phage is prepared from cultures of positive colonies and used to transform the JM 103 cells. The DNA from the resulting plates is then sequenced by using the termination procedure of the dideoxy chains. The nucleotide sequence confirms that a mutation in the desired position of the gene has been obtained.

The fragment of the mutated $\alpha_1$-AT gene, BglII-PstI, is then cleaved from the genome of M13 and transferred into the expression plasmid pTG983 after excision of the BglII/PstI fragment. This manipulation results in a plasmid pTG999 identical with pTG983 with the sole difference that the gene coding for the $\alpha_1$-AT includes a mutation at the level of the fixation site of the elastase.

Expression of [Val$^{358}$] $\alpha_1$-AT *in E. coli*

The expression of the modification at the level of the fixation site of the elastase (pTG999) is compared directly with pTG983. It is established that the synthesis level and the biological activity of the $\alpha_1$-AT is comparable in the two clones.

The semi-logarithmic culture phase (about 10$^8$ cells/ml) of pTG983, pTG999 and pTG951 (negative control corresponding to PTG983 in the gene coding for $\alpha_1$-AT) placed in growth at 28° C., is induced by heating to 37° C. for 5 hours. This inactivates the repressor c1857 coded by the host which at low temperature represses the expression of the gene of thee $\alpha_1$-AT by blocking the transcription from the promoter PL. After harvesting, the resuspended cells are ground by sonication, the debris removed by centrifugation and the concentration of protein of the supernatant liquor is estimated by a standard technique (Biorad).

The $\alpha_1$-AT level in each of the extracts is determined by radial immune diffusion (RID) by using a kit (Calbiochem-Behring). The diameter of the ring of the immune precipitate is proportional to the concentration of the antigen in the sample which is calculated by comparison with a series of standard serum dilutions.

This test shows that pTG983 and pTG999 produce $\alpha_1$-AT at levels of 0.65 and 0.55% of the total cell proteins.

Aliquot parts of the supernatant liquor obtained after sonication are also used to compare the anti-elastase activity of the $\alpha_1$-AT produced by pTG983 and pTG999. This is carried out by testing the possibility presented by the extracts of inhibiting the cleavage of methoxy-succinyl-ala-ala-pro-val-nutroanilide by human leucocyte elastase (Elastin Products Inc.). The inhibition curves of the elastase are shown in FIG. 2 and demonstrate clearly that pTG983 and pTG999 produce active forms of $\alpha_1$-AT. This observation is important since it demonstrates that the variant form of the $\alpha_1$-AT with valine in place of methionine at the level of the fixation site of elastase is active like the natural molecule.

From these curves it has been possible to calculate that pTG983 and pTG999 produce $\alpha_1$-AT at levels of 0.8 and 0.7% respectively (assuming that under these conditions 50 ng of elastase are inhibited 50% by 50 ng of $\alpha_1$-AT).

EXAMPLE 2—[Arg$^{358}$] $\alpha_1$-AT

Replacement of the codon met by arg in the gene $\alpha_1$-AT is effected in the same manner as that previously described. The change from met to arg necessitates the replacement of a nucleotide (ATG gives AGG):

|  | ala | ile | pro | MET | ser | ile |
|---|---|---|---|---|---|---|
| Original sequence: | GCC | ATA | CCC | ATG | TCT | ATC |
|  | ala | ile | pro | ARG | ser | ile |
| Mutated sequence: | GCC | ATA | CCC | AGG | TCT | ATC |

The oligonucleotide used to carry out this mutagenesis is: 5'-ATAGACCTGGGTATG-3'. This oligonucleotide is complementary with the reactive region of $\alpha_1$-AT but contains an arginine codon in place of the methionine codon.

The direct mutagenesis of the site is carried out on the gene of the cloned $\alpha_1$-AT in M13mp701 as has previously been described. After identification of the mutants by hybridization with the preceding oligonucleotide, the mutation is confirmed by sequencing of the DNA.

The variant gene of the $\alpha_1$-AT on a BglII-PstI fragment is then taken up from the genome of M13 and transferred into the expression vector pTG983 after excision of Bs1II/PstI fragment. This leads to a plasmid pTG1900 identical with pTG983 except for the mutated sequence at the reactive site.

*Expression of Modified* [FArg$^{358}$] $\alpha_1$-AT in *E. coli*

The $\alpha_1$-AT produced by pTG1900 is compared directly with that obtained through pTG983. It was possible to establish that these two clones lead to the production of proteins which react identically in a radial immune diffusion test (RID) for $\alpha_1$-AT.

The $\alpha_1$-AT variant does not show any detectable anti-elastase activity and is a very efficient inhibitor of thrombin.

Extracts subjected to sonication in induced cultures of *E. coli* TGE900 containing pTG1900 and pTG983 are prepared and the proportion of $\alpha_1$-AT in each of the extracts is determined by RID. Each extract contains an immuno-reactive material and tests indicate that in each case the expression ratio is of the order of 1% of the total cell proteins of *E. coli*.

Aliquot parts of these extracts are also used to compare the anti-elastase and anti-thrombin activity of the $\alpha_1$-AT produced in each case. The anti-elastase activity is assayed by measuring the possibilty for the extracts of inhibiting the cleavage of methoxy-succinyl-ala-ala-pro-val-p-nitroanilide by human leucocyte elastase. The inhibition curves of the elastase indicated, on the contrary to what is observed for pTG983, pTG1900 does not show any anti-elastase activity (FIG.3).

The anti-thrombin activity is assayed by measuring the ratio of inhibition of cleavage of the chromozyme TH (tosyl-gly-pro-arg-p-nitranilide-acetate) (Boehringer/Mannheim) by bovine thrombin. 4 µg of thrombin are pre-incubated at 37° C. for 20 minutes with aliquot parts of the bacterial extracts before adding the substrate up to 0.1 mM. The reaction speed is conveyed by measuring the change in ratio of the absorbance at 410 nm. The results (FIG.4) indicate under these conditions that extracts of pTG983 do not contain any detectable anti-thrombin activity, whilst the extracts of pTG1900 effectively inactivate the thrombin.

Figure 5:
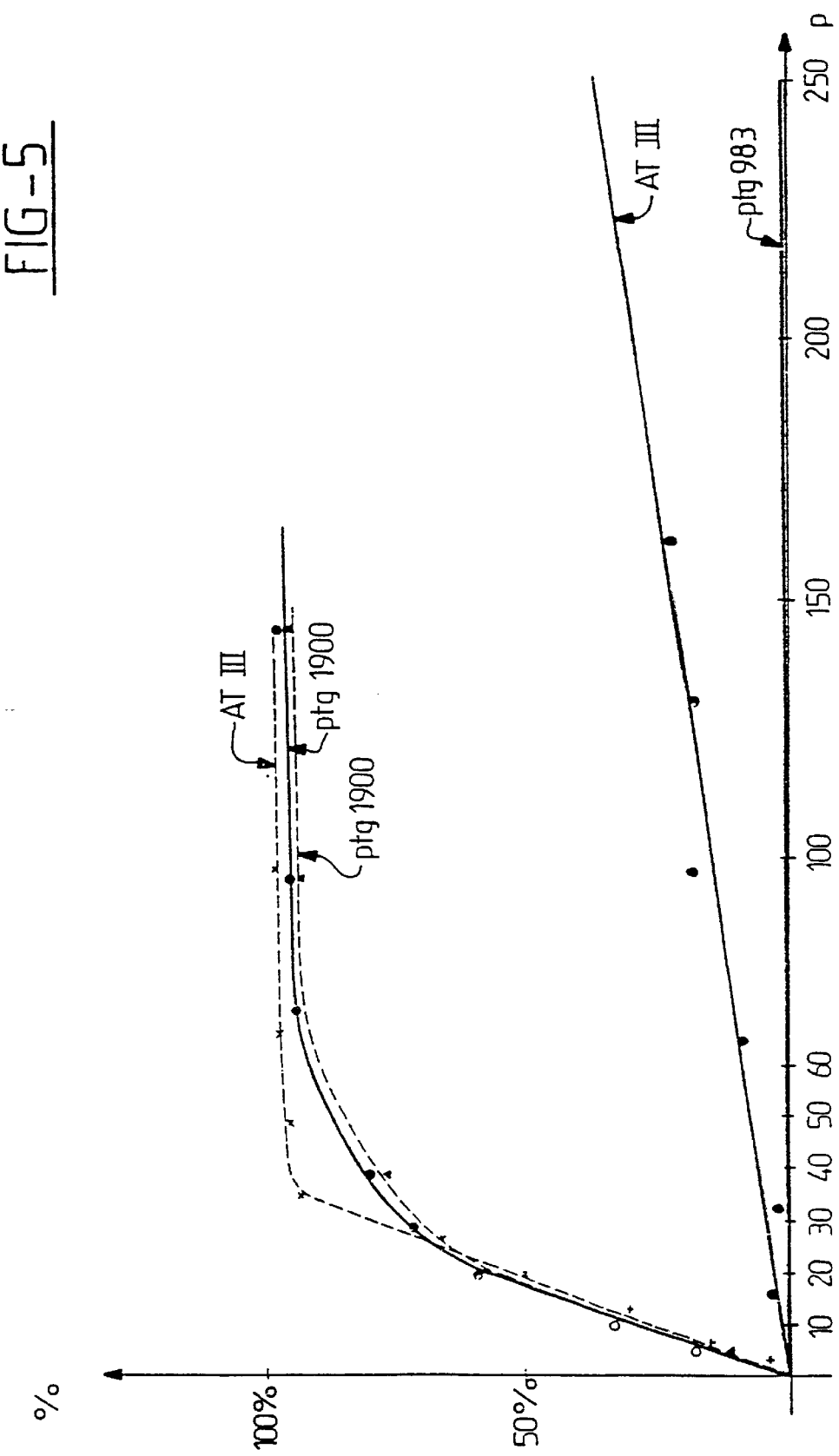
FIG. 5 shows the comparative anti-thrombin activity of extracts of *E. coli*/pTG1900 of AT-III and of AT-III in the presence of heparin.

Comparisons of these data with the AT-III inhibition curves indicate that the variant $\alpha_1$-AT has an anti-thrombin activity 15 to 20 times greater than that of AT-III in the absence of heparin and approximately the same activity (in moles) as AT-III in the presence of heparin (FIG.5).

Preparation of pTG983

The preparation of the plasmid pTG983 is described in European patent application n° 84 400126, it will be briefly recalled below.

The preparation of the plasmid pTG983 starts from the plasmid pTG907 and from the phage M13tg912 whose preparation is itself described in European patent n° 0 094 887 in the name of Applicant.

The BamHI/SphI fragment of pTG907, the BglII/HpaI fragment bearing cIIrbs and lacz' of M13tg912 and the phosphorylated adaptor HgaI/SphI were prehybridized in a molar ratio of 1:2:1 and then treated with the ligase $T_4$. Aliquot parts are used to transform the competent cells of the strain 6150 at 30° C.

The interesting cells are identified by selecting the transformants with a fragment cIIrbs/lacZ' labelled with $P^{32}$ and the structure obtained is confirmed by an enzymatic restriction study.

In order to have a first indication showing that the various elements of the expression system behave as desired, the plasmid obtained, pTG908, is transferred into a host strain N6437 which possesses both c1857 and the ω fragment of the β-galactosidase complementing the α fragment which is coded by the plasmid.

Transformants obtained placed on a dish containing IPTG+ Xgal are white at 28° C. then change to blue about 30 minutes after when they are transferred at 42° C.

This plasmid pTG908 has been used to express the gene of human $\alpha_1$-AT obtained by known techniques and described previously.

The cDNA clone of the human $\alpha_1$-AT used, pTG603, contains a single restriction site BamHI immediately after the codon for the first amino-acid of the mature protein. The coding capacity for the whole mature polypeptide, with the exception of the initial glutamic acid, is thus contained in a fragment BamHI/PstI which has been cloned on the expression vector pTG920; in this construction, the transcription is carried out from the left hand λ promoter, $P_L$, and the translation is initiated at the ATG of λ cIIrbs which, accompanied by the fixation site of the ribosomes and the 39 first pb of the gene λ cII, are fused to the beginning of the lacZ' gene as indicated.

A coupling region comprising single restriction sites is situated at the junction of cII and the sequence lacZ'. Plasmid pTG920 is a derivative of pTG908 prepared previously in which the original fragment BamHI/PstI is situated at 40 bp downstream from the ATG of the cII in pTG908 is replaced by a fragment BglII/PstI of M13tg115, as described in FIG. 6.

By means of this process, a BamHI site is obtained which is placed in the same translation phase as the BamHI site of the genes $\alpha_1$-AT.

Figure 6:
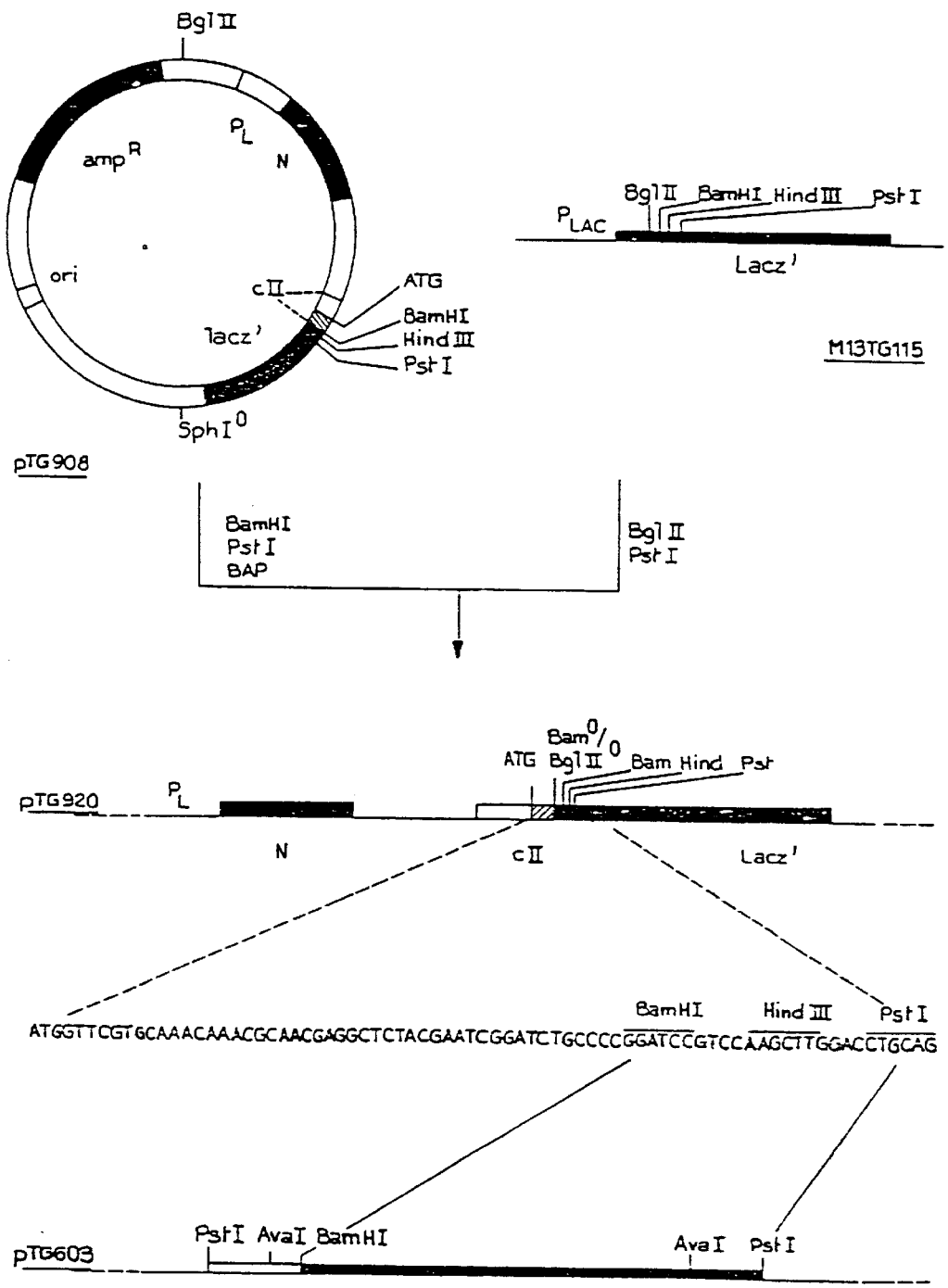
FIG. 6 shows diagramatically the preparation of pTG920.

FIG. 6 shows the cloning strategy enabling the preparation of plasmid pTG920 from the plasmid pTG908 and the phage M13tg115 and indication of the fragment to be cloned of pTG603. The full lines represent sequences coding for a protein and in the case of pTG603 represent the sequence coding for the mature polypeptide of $\alpha_1$-AT. The hatched regions represent the regions coding for the 13 N-terminal amino-acids of cII which will finally be fused with the $\alpha_1$-AT.

Thus, the insertion of a BamHI/PstI fragment of pTG603 between BamHI and the PstI site of pTG920 will lead to the expression of a fused polypeptide containing (from the NH$_2$ terminal) 13 amino-acids of the cII protein, 4 amino-acids derived from the sequence of the adaptor and the mature polypeptide of $\alpha_1$-AT, except for the glutamic acid of the terminal NH$_2$.

pTG920, treated with BamHI/PstI and alkaline phosphatase, is coupled with pTG603, digested with BamHI and PstI. The transforming TGE900 cells bearing the $\alpha_1$-AT fragment are isolated after enzymatic restriction study. One of these clones is pTG922. The detailed preparation of this clone is described in the article of Courtney et al. (1984).

The pTG922 plasmid is subjected to a complete restriction with restriction enzymes NdeI (New England Biolabs) and BamHI (Bethesda Research Labs) by using the conditions which are indicated by the supplier.

By known processes non phosphorylated complementary adapter oligonucleotides having the following structure:

5'-dTATGGAG-3' and 5'-dGATCCTCCA-3' are synthesized.

These oligonucleotides are prehybridized then subjected to ligation at 4° C. with the plasmid pTG922 which has been subjected to enzymatic restriction in a molar ratio of 50:1 using ligase DNA under known conditions (FIG. 7).

The ligation mixture is used to transform the competent cells of the strain TGE900 and the transformants obtained are spread on a culture medium in the presence of ampicillin.

The colonies are selected on nitrocellulose filters by hybridization with a probe labelled with T polynucleotide kinase 5'-dCCTGGGATCCTCCA-3'. This probe entirely complements the unfused construction which it is desired to select but only complements 7 of the nucleotides of the pTG922 parent plasmid, this is insufficient to ensure hybridization.

Thus, 6 positive candidates are obtained of which one is called pTG929.

The plasmid pTG929 only produces small amounts of $\alpha_1$-AT (less than 0.1% of the total cell proteins). So as to increase the expression level, CIIrbs is replaced by a synthetic rbs site: 1

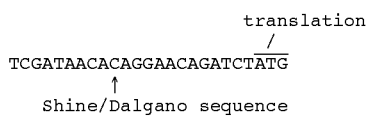

Shine/Dalgano sequence

0

Figure 8:
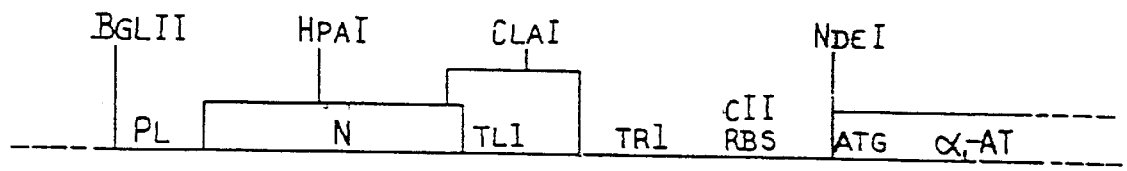
FIG. 8 shows diagramatically the preparation of pTG956.

This exchange is carried out as shown in FIG. 8.

The HpaI and BF1II sites of pTG929 are replaced by using synthetic inserts through sites ClaI and XhoI respectively.

The synthetic rbs (synth rbs) is then inserted between the NdeI site and the new ClaI site created in the N gene.

This manipulation eliminates cIIrbs and results in a truncated N gene immediately followed by synth rbs. A termination codon of the translation (TAA)into synth rbs blocks the translation of N. The plasmid obtained is pTG956.

In the plasmid pTG956 the original sequence of $\alpha_1$-AT is replaced by a, mutated sequence: 1

```
                      met glu asp pro glu gly asp ala
original sequence : ATG GAG GAT CCC CAG GGA GAT GCT met glu asp pro glu gly asp ala
mutated sequence  :ATG GAA GAT CCT CAA GGC GAT GCT
                           *       *   *   *
```
0

Each change (noted by an asterisk) is effected at the 3 position of the codons and does not modify the amino-acid coded. The gene of the $\alpha_1$-AT was modified by using the mutagenesis technique directed to sites by using a synthetic oligonucleotide which defines the particular base changes.

The sequence changes selected come from a statistical study which demonstrates a preference for certain bases in several positions in the vicinity of the beginning of the *E. coli* genes.

These changes will also destabilize the regions corresponding to possible secondary structures which may appear in the mARN sequence of the $\alpha_1$-AT. The oligonucleotide for the mutagenesis is:

5'-AGCATCGCCTTGAGGATCTTCCAT-3'

This sequence contains 4 differences with respect to the original sequence and results in the modifications indicated previously in the gene of $\alpha_1$-AT.

The plasmid obtained, PTG983, is identical with PTG956 except for the previously mentioned changes.

EXAMPLE 3

Preparation of the Variant [Gly$^{358}$] of $\alpha_1$-AT

This variant is constructed by direct mutagenesis of the site, by means of a synthetic oligonucleotide, like that which was described in example 1.

In this case, the oligonucleotide used bearing the desired mutation is the following:

5'-GATAGAACCGGGTATGGC 3'

This leads to the mutation ATG→GGT (Met→Gly).

As described in example 1, the mutagenesis is carried out on the gene of the $\alpha_1$-AT sub-cloned in M13mp701. After the mutation, the BG1II-PstI fragment comprising the variant gene is transfered into the expression plasmid pTG983 described in the principal patent.

By transformation of *E. coli* with this plasmid, as previously described, the expression of the variant [Gly$^{358}$] of the $\alpha_1$-AT is obtained.

EXAMPLE 4

Preparation of the Variants [Leu$^{358}$], [Ala$^{358}$], [Ile $^{358}$] and [Phe$^{358}$] of $\alpha_1$-AT The different variants mentioned previously are prepared by replacement of a suitable fragment of DNA in the gene of the $\alpha_1$-AT.

Figure 9:
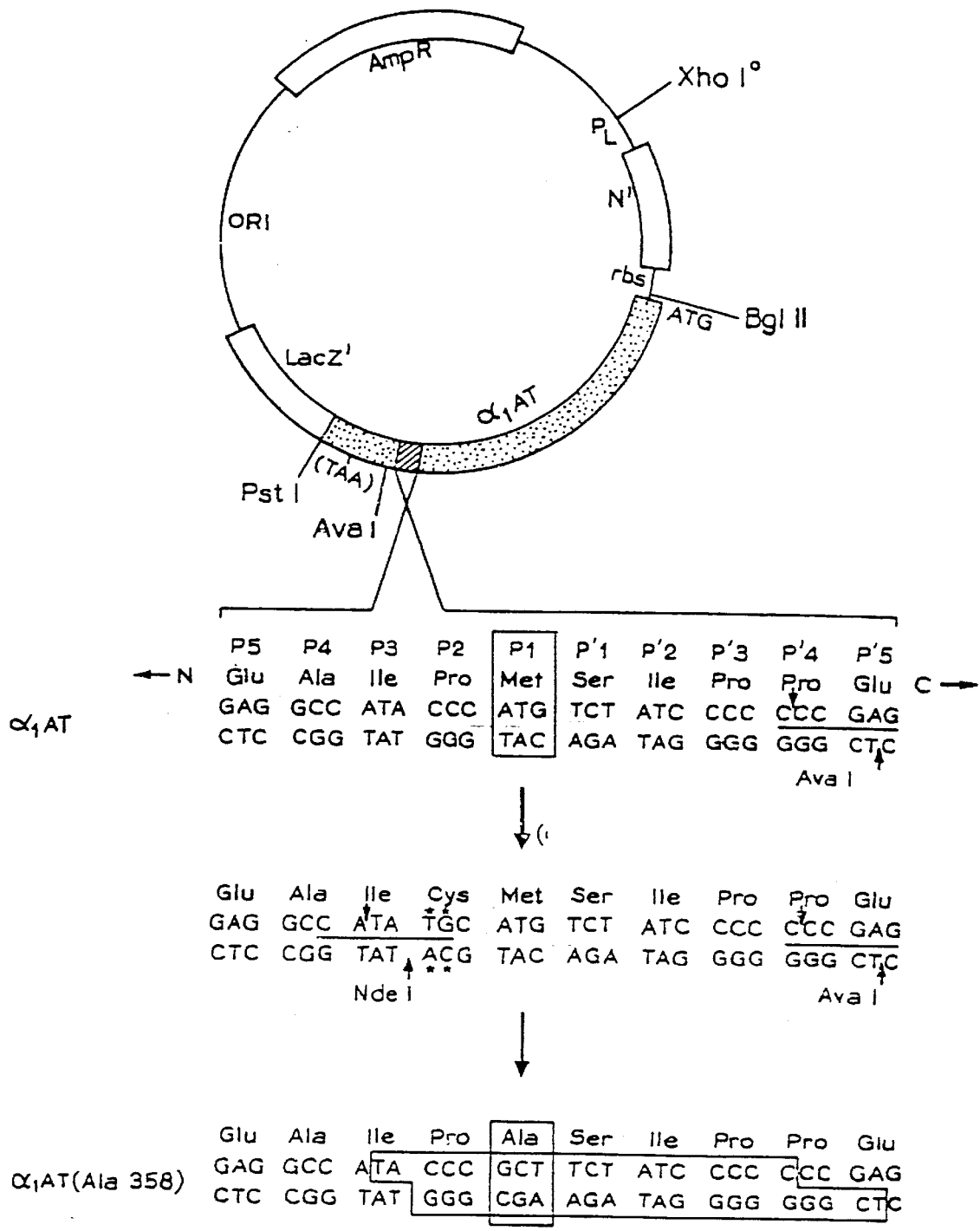

The principle of the technique is described in the accompanying FIG. 9.

The variants are constructed by replacing a small DNA segment at the level of the region coding for the amino acid 358 by a double-strand synthetic fragment containing the appropriate mutation.

The small fragment is cleaved from the gene using restriction enzymes NdeI and AvaI which cut on each side of the region coding for the active site of the $\alpha_1$-AT.

The AvaI site already exists in the original gene but a new site NdeI must be created for the working of the process; this is carried out by a directed mutation of the site by a synthetic oligonucleotide (example 1).

After treatment by the restriction enzymes, the plasmid deleted from the region coding for the active site is separated by preparative electrophoresis on gel and treated with veal intestine phosphatase, then this preparation is coupled, by using ligase T4, with a small synthetic DNA fragment containing the desired mutation as well as sequences forming single-strand 5' extensions corresponding to those of the gene cut by NdeI and AvaI.

This methodology leads to structures identical with that of pTG983, except for mutations at the level of the active site.

Each of the variants is produced in *E. coli* with levels which are in the vicinity of those obtained for pTG983 described in the principal patent, as emerges radial immunodiffusion tests, that is to say at levels of about 1% of the total cell proteins of *E.coli*.

The sonicated and clarified extracts are tested for the presence of inhibiting activity of human neutrophil elastase or of cathepsin G.

The results obtained are collected in FIGS. 10 and 11 appended, the inhibition of the elastase being measured like that described in example 2 and the cathepsin G activity being measured by using a chromogenic substrate, N-succinyl-ala-ala-pro-phe-p-nitroanilide.

The variants [Leu 358], [Ala 358] and [Ile 358] inhibit elastase activity like the variants [Met 358] and [Val 358] whilst the variants [Gly 358] and [Arg 358] do not do so.

Of all the variants tested, only the variants [Leu 358] and [Met 358] inhibit cathepsin G.

Treatment with 10mM N-chlorosuccinimide (NCS), of which the results are illustrated in FIG. 12, show that under the conditions where the variant, [Met 358] (FIG. 12*a*) is completely inactivated by oxidation, the variants, [Leu 358] (FIG. 12*b*), [Ala 358 (FIG. 12*c*), [Ile 358] (FIG. 12*d*) and [Val 358] (FIG. 12*e*) remain fully active against neutrophil elastase.

EXAMPLE 5

Production of Truncated Variants of $\alpha_1$-AT

These variants are prepared in the following manner, illustrated by FIG. 13:

The plasmid pTG983 is used to start with; and it is mutated by means of a synthetic oligonucleotide so as to create a single Apai site around the codon 8 by replacing the two CT nucleotides of the codon 7 by GG nucleotides.

Then, a further mutation of the plasmid is effected to create an NdeI site at the level of the initiation codon of the translation.

The resulting plasmid is treated with enzymes Apai and NdeI so as to delete the portion corresponding to the amino acids which it is desired to truncate.

This deleted fragment is replaced by a synthetic oligonucleotide which permits the fusion of the 6th codon of the $\alpha_1$-AT to the initiation codon to be ensured.

In order to improve the expression level of the truncated proteins, the fixation site of the ribosomes present on pTG983 was replaced by a fixation site of the synthetic ribosomes named R1 which presents the structure shown in FIG. 5 and which occurs inserted between the restriction sites ClaI and NdeI.

By transformation of *E. coli* by means of the plasmid obtained, named pTG1904R1T2, an $\alpha_1$-AT devoid of the 5 first amino acids of the N-terminal end is obtained; its expression ratio is of the order of 15% of the total cell proteins of *E. coli*.

This expression is measured by densitometric reading of an electrophoresis gel colored with Coomassie blue.

The sonicated and clarified supernatant liquors of the induced cells contain the truncated $\alpha_1$-AT; the latter effectively inhibits human neutrophil elastase.

A good correlation is observed between the determination by radioimmunodiffusion and the anti-elastase activity.

Taking into account the demonstration of this activity of certain truncated derivatives, the present invention extends also to pharmaceutical compositions and to biological reagents containing them, particularly to the reagents useful for the determination of neutrophil elastase and of thrombin.

REFERENCES

KURACHI et al., Proc. Natl. Acad. Sci. USA, 78, 6826–6830 (1981).

CHANDRA et al., Biochem. Biophys. Res. Comm., 103, 751–758 (1981) COURTNEY et coll., Proc. Natl. Acad. Sci. USA, 81, 669–73 (1984).

What is claimed is:

1. A protein which has an amino acid sequence consisting of the amino acid sequence of human $\alpha_1$-antitrypsin wherein the natural methionine residue of position 358 is replaced by a leucine residue.

* * * * *